United States Patent [19]
Davis et al.

[11] Patent Number: 5,351,694
[45] Date of Patent: Oct. 4, 1994

[54] NONINVASIVE-BLOOD-PRESSURE (NIBP) MONITORING APPARATUS WITH NONINFLATABLE, PRESSURE-INFORMATION-PROVIDING (PIP) STRUCTURE

[75] Inventors: Charles L. Davis; John R. Marshall, both of Beaverton, Oreg.

[73] Assignee: Protocol Systems, Inc., Beaverton, Oreg.

[21] Appl. No.: 977,597

[22] Filed: Nov. 16, 1992

[51] Int. Cl.$^5$ .............................................. A61B 5/021
[52] U.S. Cl. ..................................... 128/672; 128/686; 128/687
[58] Field of Search ............... 128/672, 677, 680–686, 128/689–690, 715, 903, 687; 606/201–203

[56] References Cited

U.S. PATENT DOCUMENTS

| | | | |
|---|---|---|---|
| 2,753,863 | 7/1956 | Bailey | 128/686 X |
| 3,090,377 | 5/1963 | Salisbury et al. | 128/677 |
| 3,095,873 | 7/1963 | Edmunds, Jr. | 128/686 |
| 3,535,067 | 10/1970 | Lesher et al. | 128/672 |
| 3,704,708 | 12/1972 | Iberall | 128/686 X |
| 3,935,984 | 2/1976 | Lichowsky et al. | 128/686 |
| 4,206,765 | 6/1980 | Huber | 128/677 |
| 4,248,241 | 2/1981 | Tacchi | 128/686 X |
| 4,274,424 | 6/1981 | Kimura et al. | 128/686 |
| 4,406,289 | 9/1983 | Wesseling et al. | 128/690 X |
| 4,441,504 | 4/1984 | Peterson et al. | 128/686 |
| 4,564,020 | 1/1986 | Link | 128/677 |
| 4,799,491 | 1/1989 | Eckerle | 128/672 |
| 4,889,133 | 12/1989 | Nelson et al. | 128/681 |

*Primary Examiner*—Angela D. Sykes
*Attorney, Agent, or Firm*—Kolisch Hartwell Dickinson McCormack & Heuser

[57] ABSTRACT

Noninvasive-blood-pressure (NIBP) monitoring apparatus is disclosed which is usable to perform either oscillometric or auscultatory NIBP. The apparatus includes relatively adjustable, noninflatable, pressure-information-providing (PIP) structure usable to apply NIBP-useful pressure to such limb adjacent such vessel. Also included is pressure-changer structure associated with the PIP structure, and operable to adjust the same to a beginning NIBP-useful pressure, and to subsequent NIBP-useful pressures, with such adjustment effecting the availability of pressure information that can be sensed by such sensor structure. The apparatus is preferably constructed for oscillometric NIBP monitoring and includes a reaction band removably fittable on and circumscribingly about the limb of such living subject. The preferred construction is for portable, self-contained, ambulatory usage. Other embodiments include providing an output communicator for sending NIBP-data signals in various outputs including electrical, wireless and optical, and visually perceptible ones.

12 Claims, 2 Drawing Sheets

NONINVASIVE-BLOOD-PRESSURE (NIBP) MONITORING APPARATUS WITH NONINFLATABLE, PRESSURE-INFORMATION-PROVIDING (PIP) STRUCTURE

BACKGROUND OF THE INVENTION

The present invention relates to blood-pressure monitors, and more particularly to noninvasive-blood-pressure (NIBP) monitoring apparatus with relatively adjustable, noninflatable, pressure-information-providing (PIP) structure.

Conventional noninvasive-blood-pressure (NIBP) monitoring apparatus includes a cuff-inflation/deflation system to apply occluding pressure to a subject's blood vessel, and ultimately to measure blood-pressure parameters from sensed changes in an associated blood-pressure cuff used to apply such pressure. Sometimes disappointingly, the design of such NIBP apparatus, as embodied in prior art systems, often involves unwanted costs and complexities relative to valving and pressure-fluid-flow management to and from the inflatable cuff. For example, conventional monitors include pumps, valves and pneumatic hoses. Further complexities are introduced in some instances with the requirement for relatively extensive electrical "tethering" of such apparatus to external equipment for acquiring diagnostic data.

Accordingly, it is a principal object of the present invention to provide NIBP monitoring apparatus that overcomes the disappointments and inefficiencies, such as those just mentioned, associated with such conventional monitors.

Another object is to provide such apparatus which features a non-inflatable device for applying occluding pressure to a subject's blood vessel.

A still further object is to provide apparatus of the type mentioned that is essentially completely self-contained, free-standing, and ambulatory, and that does not require any sort of physical tethering to external equipment.

Yet another object is to provide such apparatus that accomplishes proper vessel occlusion to acquire blood-pressure data.

It is also an object of the invention to provide apparatus as outlined that can be manufactured easily and cost-effectively.

SUMMARY OF THE INVENTION

The invention achieves the above objects by providing noninvasive-blood-pressure (NIBP) monitoring apparatus which is usable to perform either oscillometric or auscultatory NIBP. The apparatus includes relatively adjustable, noninflatable, pressure-information-providing (PIP) structure usable to apply NIBP-useful pressure to such limb adjacent such vessel. Also included is pressure-changer structure associated with the PIP structure, and operable to adjust the same to a beginning NIBP-useful pressure, and to subsequent NIBP-useful pressures, with such adjustment effecting the availability of pressure information that can be sensed by such sensor structure.

The apparatus is preferably constructed for portable, self-contained, ambulatory, oscillometric NIBP monitoring. That construction includes a reaction band removably fittable on and circumscribingly about the limb of such living subject.

In the preferred embodiment, the PIP structure may be thought of as pulse-responsive structure. The pulse-responsive structure may be made with a pad-like construction, such as that of a fluid-filled, non-inflatable bladder. The bladder may be constructed with plural subregions, each having a sensor operatively associated with it, with the subregions/sensors providing plural streams of NIBP-data signals.

Continuing with a summary of the preferred embodiment, the pulse-responsive structure is operable, with the band fitted in place, to pressure-contact such limb adjacent such vessel. Power-operated structure interposes the band and pulse-responsive structure to adjust bidirectionally the latter for imposing and relaxing NIBP-useful pressure on tile vessel. Sensor structure is operatively associated with the pulse-responsive structure for sensing therethrough heartbeat-induced pressure pulsations in the vessel, and for generating related NIBP-data signals.

The reaction band includes frame structure releasably fittable on a person's limb and providing a mounting framework for the pulse-responsive structure. A change-condition adjustment mechanism is carried on the frame structure and operatively connected to the pulse-responsive structure for adjusting the latter selectively and differentially, thereby imposing and relaxing NIBP-useful pressure on such a vessel.

The power-operated structure and an associated power source are on-board the frame structure, and operatively connected to the adjustment mechanism for operating the same. Control means are also provided for controlling the operation of the power-operated structure, and for receiving the NIBP-data signals generated by the sensor.

The frame structure is constructed for lateral fitment on a subject's limb, and when in place, at least partially circumsurrounds the same. Also, the adjustment mechanism is constructed to impose and relax occluding pressure on the target blood vessel, and the power-operated structure includes a stepper motor.

Other embodiments include providing an output communicator for sending NIBP-data signals in various outputs including electrically, wireless and optical, and visually perceptible ones.

These and additional objects and advantages of the present invention will be more readily understood after a consideration of the drawings and the detailed description of the preferred embodiment.

DETAILED DESCRIPTION OF THE PREFERRED EMBODIMENT AND BEST MODE OF CARRYING OUT THE INVENTION

Figure 1:
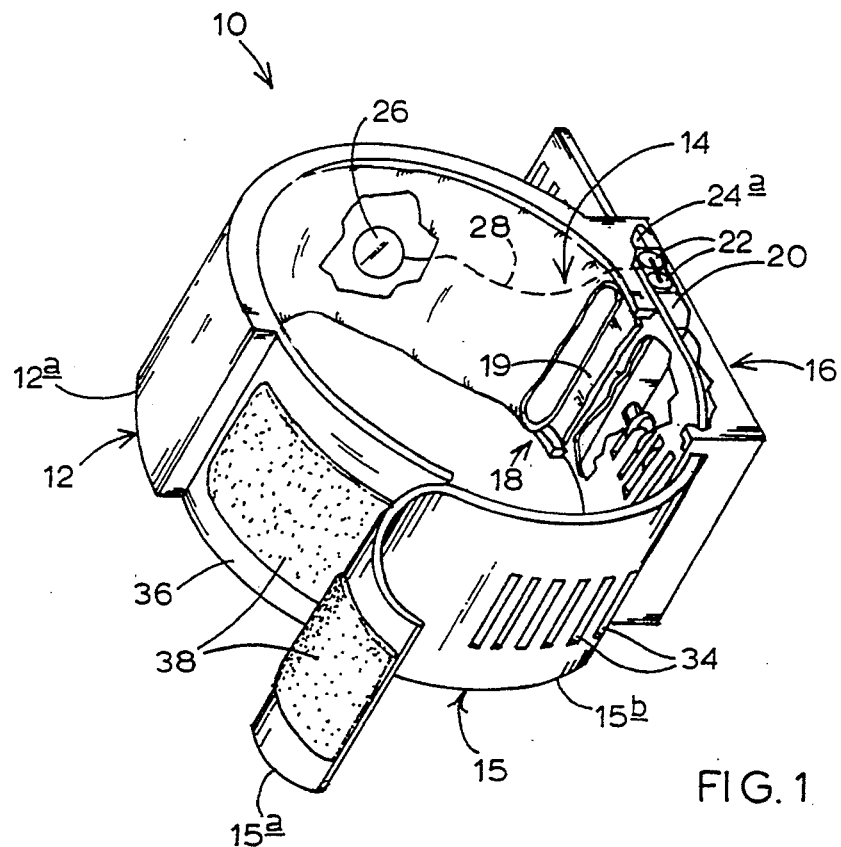
FIG. 1 is an isometric view of oscillometric NIBP monitoring apparatus, made in accordance with the preferred embodiment of the present invention, for portable, self-contained, ambulatory usage, and shown with certain portions broken away to show detail.

Referring to FIG. 1, the invented NIBP monitoring apparatus is shown at 10 being constructed according to its preferred embodiment for portable, self-contained, ambulatory usage to perform oscillometric NIBP. A few things should be understood from the outset of this description. First, while describing its use in connection with oscillometric NIBP, the invention is readily usable to perform auscultatory NIBP as will be described below. Second, it should be understood that apparatus 10 is designed for oscillometric NIBP measurement according to well-known principles for such measurement. The details of such measurement will not be described herein because they are adequately described in U.S. Pat. No. 4,889,133, which description is incorporated herein by reference.

Apparatus 10 is for (1) reversibly applying pressure adjacent a subject's limb as a way of relaxably constricting blood flow in an associated blood vessel, and (2) producing ultimately pressure information relative to such vessel that can be sensed by sensor structure associated with such apparatus. As will be described further below, apparatus 10 includes relatively adjustable, non-inflatable, pressure-information-providing (PIP) structure 14 which is usable to apply NIBP-useful pressure to such limb adjacent such vessel. Also included is pressure-changer structure 16 associated with the PIP structure, and operable to adjust the same to a beginning NIBP-useful pressure, and to subsequent NIBP-useful pressures, with such adjustment effecting the availability of pressure information that can be sensed by such sensor structure.

Now referring to particulars in FIG. 1, apparatus 10 includes a reaction band 12 including frame structure 12a adapted for a removable, circumferential fit around a limb 13 (FIG. 4) of a living subject, adjacent a blood vessel (undepicted) within such limb. Associated with band 12 is PIP structure 14 which is also referred to herein as pulse-responsive structure to describe its use in connection with oscillometric NIBP as will be described. PIP structure 14 is operable with the band fitted in place to pressure-contact the limb adjacent the blood vessel.

Figure 2:
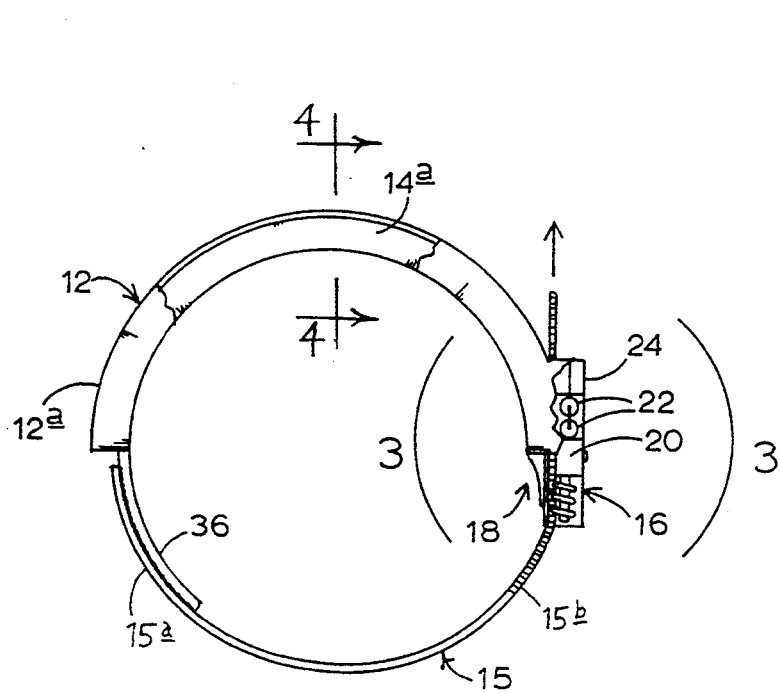
FIG. 2 is an axial view of the apparatus of FIG. 1, also with certain portions broken away to illustrate detail.
Figure 7:
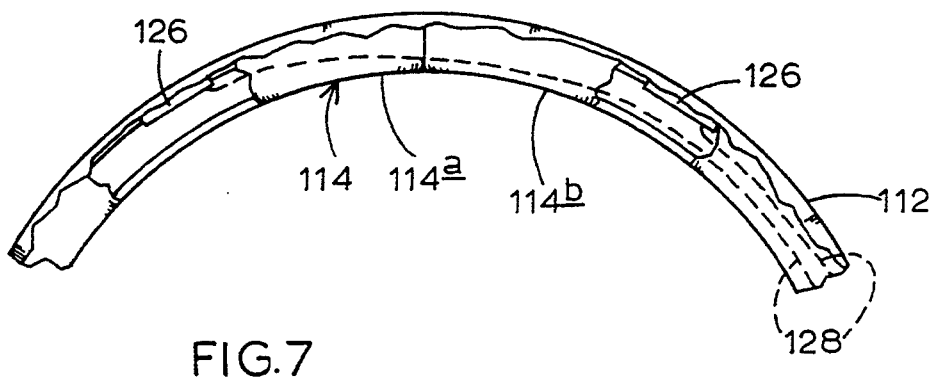
FIG. 7 is similar to FIG. 2 and shows, on an enlarged scale, a fragmentary axial view of a second embodiment of the invention.

Referring to FIG. 2, the preferred construction of pulse-responsive structure 14 is that it be formed pad-like, such as being formed as a fluid-filled bladder with a to-be-described sensor operatively associated with it for ultimately providing a stream of NIBP-data signals. Referring for a moment to FIG. 7, pulse-responsive structure 14 may also be constructed with plural subregions (i.e. subregions 114a, 114b of FIG. 7) each having the to-be-described sensor operatively associated with it for ultimately providing plural streams of NIBP-data signals. The presently preferred fluid for the bladder is a saline solution because the inventors believe such solution will provide the optimal load energy coupling between the ultimate blood-pressure signal source, i.e. the subject's cardiovascular system, and the to-be-described transduction mechanism. It should be understood that the desired fluid may be either a compressible or noncompressible one. With respect to material choice for the bladder, it is presently contemplated that a suitable synthetic material will be used.

Referring again to FIGS. 1-4, a band submember 15 of band 12 is shown with a latchable tab subregion 15a and a grabbable tongue subregion 15b. The significance of these subregions will be described below.

Figure 3:
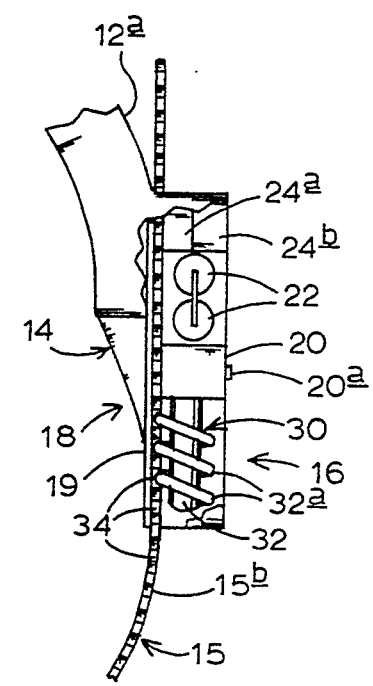
FIG. 3 is an enlarged, fragmentary detail taken generally in the area in FIG. 2 embraced by brackets indicated by reference numeral 3, further focusing on certain features shown in FIG. 2.

Still referring to FIG. 1, pressure-changer structure (also referred to as change-condition adjustment mechanism) 16 is carried on frame structure 12 and operatively connected to pulse-responsive structure 14 via suitable attachment of the pulse-responsive structure to frame structure 12a at the region identified at 18 in FIGS. 1-3.

Figure 4:
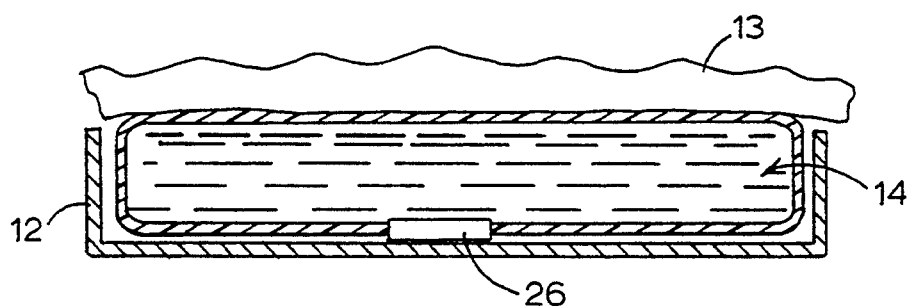
FIG. 4 is an enlarged, cross-sectional view of the apparatus taken generally along line 4—4 in FIG. 2, and after having first rotated the apparatus 180° relative to its position in FIG. 2 so that frame structure 12 would be positioned below band submember 15 rather than above it.
Figure 5:
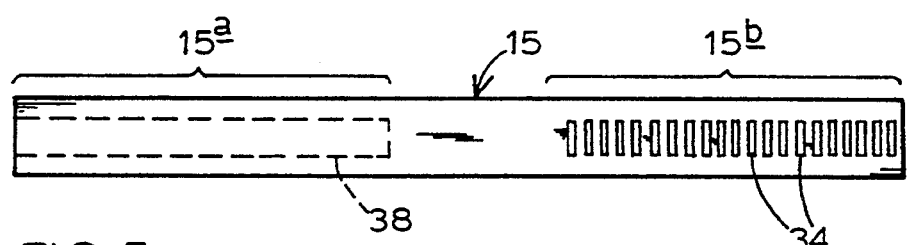
FIG. 5 is a plan view of a band member associated with the reaction band after such member has been removed and positioned flat.

As will be understood, change-condition adjustment mechanism 16 is operable selectively and differentially to adjust the pulse-responsive structure with respect to the subject's limb to impose and relax NIBP-useful pressure (preferably occluding pressure) on a blood vessel in limb 13 (FIG. 4). With respect to attachment of pulse-responsive structure 14 to frame structure 12, it should be noted that adjacent region 18 is a backing member 19 secured to and sandwiched between the two components. Backing member 19 is suitably rigid to provide support for to-be-described components of the invention that are mounted on frame structure 12a and band submember 15.

Referring to FIGS. 1-3, there are several components of the present invention coupled to an on-board frame structure 12a. First, power-operated structure, such as a motor 20, interposes band 12 and pulse-responsive structure 14. As will be described, motor 20 is operable to adjust bidirectionally the band to impose and relax NIBP-useful pressure on the vessel in the subject's limb. It should be understood that any suitable power-operated structure may be used, including pneumatically powered structure. Other components on frame structure 12a include a power source for motor 20, such as suitable batteries 22, and an output communicator which is preferably provided as a control/communication-interface module 24. It should be understood that the output communicator is shown schematically in the drawings as box-shaped members, but are in fact in communication with each other so that, for example, module 24 is operable to control motor 20. Details of module 24 will be described below. The motor may be a stepper or linear motor, and it is actuated via a suitable actuator such as button 20a (FIG. 3).

With respect to details of module 24, it includes a controls region 24a and communication-interface region 24b. The controls region is preferably constructed as a circuit board suitably connected to motor 20 and to a to-be-described sensor 26 for monitoring blood pressure. Referring to FIG. 1, the connection between sensor 26 and motor 20 is shown schematically by dashed line 28, and it may be constructed as a suitably positioned conductor. Circuit board 24a is for controlling the operation of the motor, and for receiving the NIBP-data signals generated by sensor 26. Communication-interface region 24b is coupled to circuit board 24a and preferably is constructed as a visual-display device such as an LED or LCD for displaying blood-pressure parameters determined by operation of the invention on a living subject. The communication-interface region may also be made according to one of the following, presently proposed alternative constructions:

(1) a wireless transmitter such as a radio transmitter operatively connected to circuit board 24a which accommodates selective wireless (e.g. RF) output of NIBP-data generated by sensor 26;

(2) an LED constructed for accommodating selective optical output of NIBP-data generated by sensor 26; or (3) an I/O port for receiving a conductor(s) that accommodates selectively releasable tethered output of NIBP-data signals generated by sensor 26.

Referring to FIGS. 1 and 4, sensor 26 is operatively associated with pulse-responsive structure 14 for sensing therethrough heartbeat-induced pressure pulsations in the blood vessel of the subject, and for generating related NIBP-data signals. Sensor 26 may take the form of a suitable transducer, which may be a strain gauge.

Figures 6A, 6B, 6C:
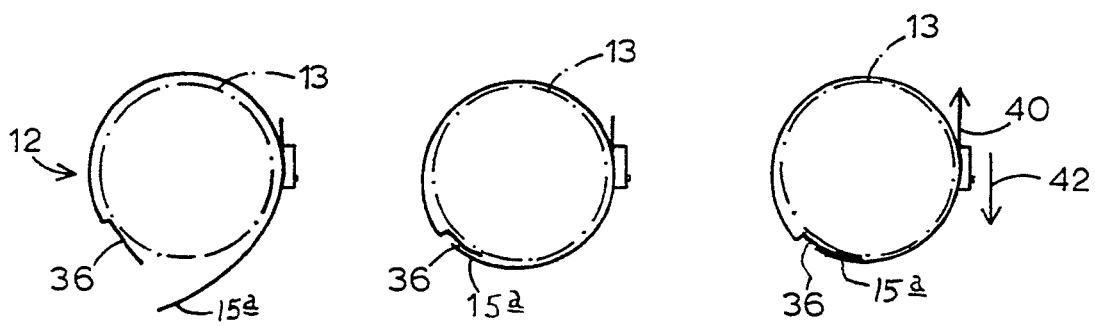
FIGS. 6A-6C show schematically three stages of attachment of the apparatus to a subject's limb, i.e. an open, to-be-attached stage (FIG. 6A), a closed stage with gross attachment around the limb (FIG. 6B) and a data-acquiring stage resulting from further, gradual, controlled fine attachment, followed by gradual, controlled release (FIG. 6C).

Now focusing on certain additional details of the apparatus of the present invention, reference is made briefly to FIGS. 6A–6C. From these views it should be understood that frame structure 12a is preferably constructed for a lateral fit on limb 13 (FIG. 4). Referring to FIGS. 6B–6C, frame structure 12a is designed to circumsurround, at least partially, limb 13.

Referring back to FIGS. 2–3, adjustment mechanism 16 includes a reversibly movable grab mechanism 30 which is operable with grabbable tongue subregion 15b to effect controlled fine adjustment during a to-be-described data-acquiring stage of operation. As will be explained, grabbable tongue subregion 15b is operatively and releasably drivingly engaged by grab mechanism 30. The grab mechanism includes a worm-gear-like device 32 with teeth 32a, which device is drivingly connected to motor 20. Tongue subregion 15b is formed with apertures 34 adapted to receive teeth 32a.

Referring to FIGS. 1, 2 and 4, the reader's attention is drawn to portions of the apparatus that provide gross attachment of the same around the subject's limb. FIG. 1 shows a flexible tab region 36 which extends from one end of frame structure 12a and is releasable attachable to band submember 15. Preferably, the topside of tab region 36 and the underside of band submember 15 are provided with matable components 38 of the well-known hook/loop fastener marketed under the trademark VELCRO. As shown best in FIGS. 2 and 6B, gross attachment of apparatus 10 around limb 13 is accomplished with such VELCRO fastener.

OPERATION

Apparatus 10 is circumscribingly placed around limb 13 by fitting band 12 around the limb, first in a closed stage with gross attachment (FIG. 6B), and then in a further, gradual, controlled fine attachment (arrow 40—FIG. 6C), followed by gradual, controlled release (arrow 42—FIG. 6C). Gross attachment is accomplished by fastening band submember 15 to tab region 36 using a VELCRO fastener. Fine attachment is accomplished by controlled operation of grab mechanism 30 to a desired threshold, such as occluding pressure. Those skilled in the art appreciate various methods of determining such desired threshold, and an example is to construct circuit board 24a with a suitable computer program that stops motor 20 from tightening band submember 15 around limb 13 when sensor 26 stops sensing heartbeat-induced pressure pulsations in bladder 14. A suitable safety mechanism (undepicted) should also be included to release actuation of the fine attachment shown in FIG. 6C by arrow 40 in cases where equipment malfunctions and the pressure applied by apparatus 10 to the subject's limb is undesirably high.

Still referring to FIG. 6C, it should now be understood that gradual controlled release of band submember 15 (arrow 42) is the data-acquiring stage of operation. During that stage, blood-pressure-signal data is sent to circuit board 24a and processed as further described in above-referenced U.S. Pat. No. 4,889,133. For even further improved processing of blood-pressure-signal data, the inventors propose using the method that is described in co-pending U.S. patent application Ser. No. 07/696,513, which disclosure is also incorporated herein by reference. The controlled release of band member 15 will cause a corresponding, controlled release in pressure applied by pulse-responsive structure 714, allowing sensor 26 to sense heartbeat-induced pressure pulsations as they occur from below systolic pressure to diastolic pressure.

With respect to using the invention to perform auscultatory NIBP, the above description is sufficient with the following additional details. The PIP structure, i.e. bladder 14, can be used to apply the necessary, controlled counterpressure to the subject's limb. Then, with the addition of sound-receiving structure, such as a stethoscope or microphone, auscultatory NIBP can be performed. The stethoscope or microphone would of course be positioned adjacent the subject's limb for identifying audibly the occurrence of a Korotkoff sound during the above-described adjustment of bladder 14. In this way, the apparatus is usable to relate to such audible occurrence with pressure information provided by the bladder.

Under the auscultatory NIBP method, bladder 14 is used to apply a counterpressure, which is sensed by sensor 26 and sent via conductor 28 to control/communication-interface module 24. As noted above, the module may include a conventional LCD or LED display for presenting pressure information in a visually perceptible format. The operator simply notes the pressure reading on the display at the time of the occurrence of the Korotkoff sound. Further details of auscultatory NIBP measurement will not be described herein because they are well-known and adequately described in U.S. Pat. No. 4,564,020, which description is incorporated herein by reference.

While the present invention has been shown and described with reference to the foregoing preferred embodiment, it will be apparent to those skilled in the art that other changes in form and detail may be made therein without departing from the spirit and scope of the invention as defined in the appended claims.

What is claimed is:

1. A portable, self-contained, ambulatory, noninvasive-blood-pressure (NIBP) monitoring apparatus adapted for a removable circumscribing fit relative to a subject's limb adjacent a blood vessel therein, comprising:

frame structure releasably fittable on a subjects limb;
plural adjustable, fluid-filled, non-inflatable bladders mounted on said frame structure and adapted, with said frame structure and band so fitted, to pressure-contact such limb adjacent such vessel;

a change-condition adjustment mechanism carried on said frame structure and operatively connected to said bladder, with said adjustment mechanism also operable selectively and differentially to adjust said bladders, thus to impose and relax occluding pressure on such a vessel;

power-operated structure, and a power source therefor, on-board said frame structure, and operatively connected to said adjustment mechanism for operating the same;

plural sensors, one corresponding to each bladder, and with each sensor being operatively associated with a corresponding bladder for sensing therethrough heartbeat-induced pressure pulsations in said pulse-responsive structure, and for generating at least two streams of related NIBP-data signals; and control means operatively connected to said power source, to said power-operated structure and to each said sensor, for controlling the operation of the power-operated structure, and for receiving the NIBP-data signals generated by the sensors.

2. The apparatus of claim 1, wherein said frame structure at least partially circumsurrounds such a limb.

3. The apparatus of claim 2, wherein said power-operated structure comprises a stepper motor.

4. The apparatus of claim 1, wherein the fluid in said bladder is noncompressible.

5. The apparatus of claim 1, wherein the fluid in said bladder is compressible.

6. The apparatus of claim 1, which further comprises, mounted on said frame structure, an output communicator which accommodates selectively releasable tethered output of blood-flow data generated by said sensor.

7. The apparatus of claim 1, which further comprises, mounted on said frame structure, an output communicator which accommodates selective radio-frequency output of blood-flow data generated by said sensor.

8. The apparatus of claim 1, which further comprises, mounted on said frame structure, an output communicator which accommodates selective optical output of blood-flow data generated by said sensor.

9. The apparatus of claim 1, which further comprises, mounted on said frame structure, an output communicator which accomodates visually perceptible display of blood-flow data generated by said sensor.

10. Oscillometric, noninvasive-blood-pressure (NIBP) monitoring apparatus adapted for a removable fit relative to a desired region of a subject's limb adjacent a blood vessel therein, comprising:

a reaction band removably fittable on and circumscribingly about such limb; relatively adjustable, noninflatable, saline-solution-filled, pulse-responsive structure associated with said band and operable, with the band fitted in place, to pressure-contact such limb adjacent such vessel, with said pulse-responsive structure being constructed with a relatively broad body with a pad-like configuration that allows at least a partial circumferential fit relative to such limb, which fit accomodates quick and accurate placement adjacent the desired region;

power-operated structure interposing said band and said pulse-responsive structure to adjust bidirectionally the latter to impose and relax NIBP-useful pressure on such vessel; and sensor structure operatively associated with said pulse-responsive structure for sensing therethrough heartbeat-induced pressure pulsations in such vessel, and for generating related NIBP-data signals.

11. The apparatus of claim 10, wherein said pulse-responsive structure is constructed with plural subregions, each having a sensor operatively associated it, the subregions/sensors providing plural streams of NIBP-data signals.

12. Portable self-contained, ambulatory, oscillometric, noninvasive-blood-pressure (NIBP) monitoring apparatus adapted for removable circumscribing fitment on a subject's limb adjacent a blood vessel therein, comprising:

frame structure releasably fittable on such limb;

relatively adjustable, noninflatable pulse-responsive structure mounted on said frame structure, and adapted with said frame structure so fitted, to pressure-contact such vessel, said pulse-responsive structure including a fluid-filled, non-inflatable bladder wherein the fluid is noncompressible and is a saline solution;

change-condition adjustment mechanism carried on said frame structure and operatively connected to said pulse-responsive structure with said frame structure fitted on such limb, and being operable selectively and differentially to adjust the pulse-responsive structure, thus to impose and relax NIBP-useful pressure on such a vessel;

power-operated structure, and a power source therefor, on-board said frame structure, and operatively connected to said adjustment mechanism for operating the same;

a sensor operatively associated with said pulse-responsive structure for sensing therethrough heartbeat-induced pressure pulsations in said pulse-responsive structure, and for generating related NIBP-data signals; and control means operatively connected to said power source, to said power-operated structure and to said sensor, for controlling the operation of the power-operated structure, and for receiving the NIBP-data signals generated by the sensor.

* * * * *